(12) United States Patent
Luanava et al.

(10) Patent No.: US 7,935,050 B2
(45) Date of Patent: *May 3, 2011

(54) ENDOSCOPE TIPS, SCANNED BEAM ENDOSCOPES USING SAME, AND METHODS OF USE

(75) Inventors: Selso Luanava, Woodinville, WA (US); Randall B. Sprague, Carnation, WA (US)

(73) Assignee: Microvision, Inc., Redmond, WA (US)

( * ) Notice: Subject to any disclaimer, the term of this patent is extended or adjusted under 35 U.S.C. 154(b) by 1054 days.

This patent is subject to a terminal disclaimer.

(21) Appl. No.: 11/679,067

(22) Filed: Feb. 26, 2007

(65) Prior Publication Data

US 2007/0244364 A1    Oct. 18, 2007

Related U.S. Application Data

(60) Provisional application No. 60/777,694, filed on Feb. 27, 2006.

(51) Int. Cl.
*A61B 1/06* (2006.01)
*G02B 26/08* (2006.01)
*G02B 26/10* (2006.01)
*G02B 26/12* (2006.01)
(52) U.S. Cl. .................... 600/182; 359/202.1
(58) Field of Classification Search ............ 359/201.2, 359/202.1, 212.1, 213.1, 224.1; 600/182, 600/342
See application file for complete search history.

(56) References Cited

U.S. PATENT DOCUMENTS

| | | | |
|---|---|---|---|
| 6,172,789 B1 * | 1/2001 | Kino et al. | 359/212.1 |
| 6,292,287 B1 * | 9/2001 | Fujinoki | 359/212.1 |
| 6,485,413 B1 * | 11/2002 | Boppart et al. | 600/160 |
| 6,765,706 B2 * | 7/2004 | Tokuda et al. | 359/220.1 |
| 6,950,692 B2 * | 9/2005 | Gelikonov et al. | 600/473 |
| 7,129,473 B2 * | 10/2006 | Ishihara et al. | 250/234 |
| 7,236,283 B2 * | 6/2007 | Kikuchi et al. | 359/224.1 |
| 7,252,634 B2 * | 8/2007 | Mizumo | 600/160 |
| 7,530,948 B2 * | 5/2009 | Seibel et al. | 600/178 |
| 7,604,590 B2 * | 10/2009 | Tokuda et al. | 600/129 |
| 7,791,009 B2 * | 9/2010 | Johnston et al. | 250/208.1 |
| 2002/0018276 A1 * | 2/2002 | Suga | 359/212 |
| 2003/0142934 A1 * | 7/2003 | Pan et al. | 385/116 |
| 2005/0020926 A1 * | 1/2005 | Wiklof et al. | 600/476 |
| 2005/0116038 A1 | 6/2005 | Lewis et al. | |
| 2006/0149134 A1 * | 7/2006 | Soper et al. | 600/182 |

* cited by examiner

*Primary Examiner* — Philip R Smith
(74) *Attorney, Agent, or Firm* — Kevin D. Wills

(57) ABSTRACT

Apparatuses and methods for scanned beam endoscopes, endoscope tips, and scanned beam imagers are disclosed. In one aspect, a scanned beam endoscope includes an endoscope tip having a scanner, an illumination optical fiber, and at least one light detection element. The illumination optical fiber may be positioned so that a beam emitted from it passes through one of the openings in the scanner. In another aspect, a scanned beam endoscope includes an endoscope tip having a handle substrate that may be attached to the scanner and include one or more vias formed therein for selectively positioning and aligning the illumination optical fiber, detection optical fibers, or both.

22 Claims, 9 Drawing Sheets

US 7,935,050 B2

ENDOSCOPE TIPS, SCANNED BEAM ENDOSCOPES USING SAME, AND METHODS OF USE

CROSS-REFERENCE TO RELATED APPLICATION

This application is based on provisional application No. 60/777,694, filed Feb. 27, 2006.

TECHNICAL FIELD

This invention relates to scanned beam systems and, more particularly, to scanned beam endoscopes.

BACKGROUND

Video endoscopes have been in general use since the 1980s for viewing the inside of the human body. Endoscopes are typically flexible or rigid devices that have an endoscope tip including an imaging unit, such as a digital camera or a scanned beam imager, configured for collecting light and converting the light to an electronic signal. The electronic signal is sent up a flexible tube to a console for display and viewing by a medical professional such as a doctor or nurse.

Scanned beam endoscopes are a fairly recent innovation, and an example of a scanned beam endoscope is disclosed in U.S. patent application Ser. No. 10/873,540 ("'540 application") entitled SCANNING ENDOSCOPE, hereby incorporated by reference and commonly assigned herewith. FIGS. 1 through 3 show a scanned beam endoscope disclosed in '540 application. As shown in FIG. 1, the scanned beam endoscope 100 includes a control module 102, monitor 104, and optional pump 106, all of which may be mounted on a cart 108, and collectively referred to as console 110. The console 110 communicates with a handpiece 112 through an external cable 114, which is connected to the console 110 via connector 116. The handpiece 112 is operably coupled to the pump 106 and an endoscope tip 120. The handpiece 112 controls the pump 106 in order to selectively pump irrigation fluid through a hose 126 and out of an opening of the endoscope tip 120 in order to lubricate a body cavity that the endoscope tip 120 is disposed within. The endoscope tip 120 includes a distal tip 118 having a scanning module configured to scan a beam across a field-of-view (FOV).

The endoscope tip 120 and distal tip 118 thereof are configured for insertion into a body cavity for imaging internal surfaces thereof. In operation, the distal tip 118 scans a beam of light over a field-of-view (FOV), collects the reflected light from the interior of the body cavity, and sends a signal representative of an image of the internal surfaces to the console 110 for viewing and use by the medical professional.

FIGS. 2 and 3 depict the distal tip 118 and a scanning module 128 of the distal tip 118, respectively, according to the prior art. Referring to FIG. 2, the distal tip 118 includes a housing 130 that encloses and carries the scanning module 128, a plurality of detection optical fibers 132, and an end cap 131 affixed to the end of the housing 130. The detection optical fibers 132 are disposed peripherally about the scanning module 128 within the housing 130. Referring to FIG. 3, the scanning module 128 has a housing 134 that encloses and supports a micro-electro-mechanical (MEMS) scanner 136 and associated components, an illumination optical fiber 138 affixed to the housing 134 by a ferrule 142, and a beam shaping optical element 140. A dome 133 is affixed to the end of the housing 130 and may be hermetically sealed thereto in order to protect the sensitive components of the scanning module 128.

In operation, the distal tip 118 is inserted into a body cavity. The illumination optical fiber 138 outputs a beam 144 that is shaped by the beam shaping optical element 140 to form a shaped beam 146 having a selected beam shape. The shaped beam 146 is transmitted through an aperture in the center of the MEMS scanner 136, reflected off a first reflecting surface 148 of the interior of the dome to the front of the scanner 136, and then reflected off of the scanner 136 as a scanned beam 150 through the dome 133. The scanned beam 150 is scanned across a FOV and reflected off of the interior of a body cavity. At least a portion of the reflected light from the FOV (e.g., specular reflected light and diffuse reflected light also referred to as scattered light) is collected by the detection optical fibers 132. Accordingly, the reflected light collected by the detection optical fibers 132 may be converted to an electrical signal using optical-electrical converters, such as photodiodes, and the signal representative of an image may be sent to the console 110 for viewing on the monitor 104.

While the scanned beam endoscope 100 is an effective endoscope, the distal tip 118 has a diameter that is typically larger than desired. It may be desirable to reduce the overall bulkiness and size of the distal tip 118 so that the size of an incision made for insertion of the distal 118 can be reduced. Reducing the size of the distal tip 118 may also be desirable to reduce patient discomfort when the endoscope is inserted into a preexisting opening in the body. Also, in some applications, it may be desirable to selectively position the illumination optical fiber 138 and/or the detection optical fibers 132 within the scanning module 128 to improve the performance characteristics of some aspects of the distal tip 118, and/or manufacturability thereof.

SUMMARY

Scanned beam endoscopes, endoscope tips, scanned beam imagers, and methods of use are disclosed. In one aspect, a scanned beam endoscope includes a light source and an endoscope tip. The endoscope tip includes an illumination optical fiber having an output end and an input end coupled to the light source. A scanner having a scan plate may be positioned to receive a beam output from the output end of the illumination optical fiber and operable to scan the beam across a FOV. The scanner includes at least one opening located in a portion of the scanner other than the scan plate. The output end of the illumination optical fiber may be positioned so that the light output from it passes through the at least one opening in the scanner. One or more light detection elements may be positioned to receive light reflected from the FOV.

In another aspect, a method of scanning light across a FOV is disclosed. The method includes transmitting a beam through an opening in a scanner located in a portion of the scanner other than a scan plate thereof, and redirecting the beam to the scan plate. The method further includes scanning the redirected beam across the FOV.

In another aspect, a scanned beam endoscope includes a light source and an endoscope tip. The endoscope tip includes an illumination optical fiber having an output end and an input end coupled to the light source. A scanner is positioned to receive a beam output from the output end of the illumination optical fiber and operable to scan the beam across a FOV. One or more detection optical fibers may be positioned to receive light reflected from the FOV. A handle substrate is attached to the scanner, and the illumination optical fiber, detection optical fibers, or both may be selectively positioned within the handle substrate. Thus, the handle substrate may function as a ferrule for holding and aligning the optical fibers of the endoscope.

In yet another aspect, a method of forming a MEMS scanner assembly is disclosed. The method includes providing a scanner attached to a handle substrate. The handle substrate has at least one via formed at least through the handle substrate. An optical fiber is inserted into the at least one via and the optical fiber is secured within the at least one via.

The teachings disclosed herein are also applicable to scanned beam imagers and bar code scanners.

DETAILED DESCRIPTION OF THE EMBODIMENTS

Apparatuses and methods for scanned beam endoscopes, endoscope tips, and scanned beam imagers are disclosed. Many specific details of certain embodiments are set forth in the following description and in FIGS. 4 through 10 in order to provide a thorough understanding of such embodiments. One skilled in the art, however, will understand that there may be additional embodiments, or that the disclosed embodiments may be practiced without several of the details described in the following description.

Figure 1:
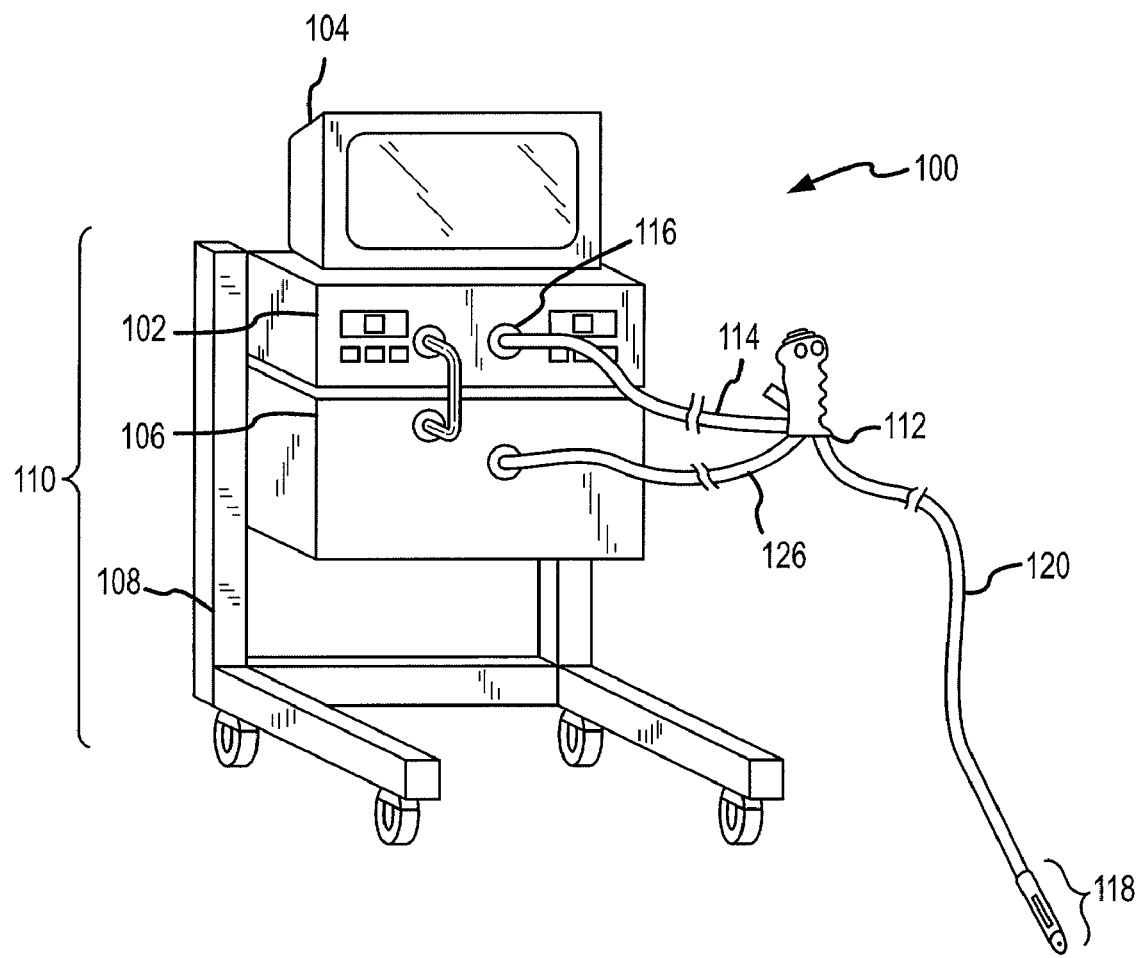
FIG. 1 is schematic drawing of a scanned beam endoscope according to the prior art.
Figure 2:
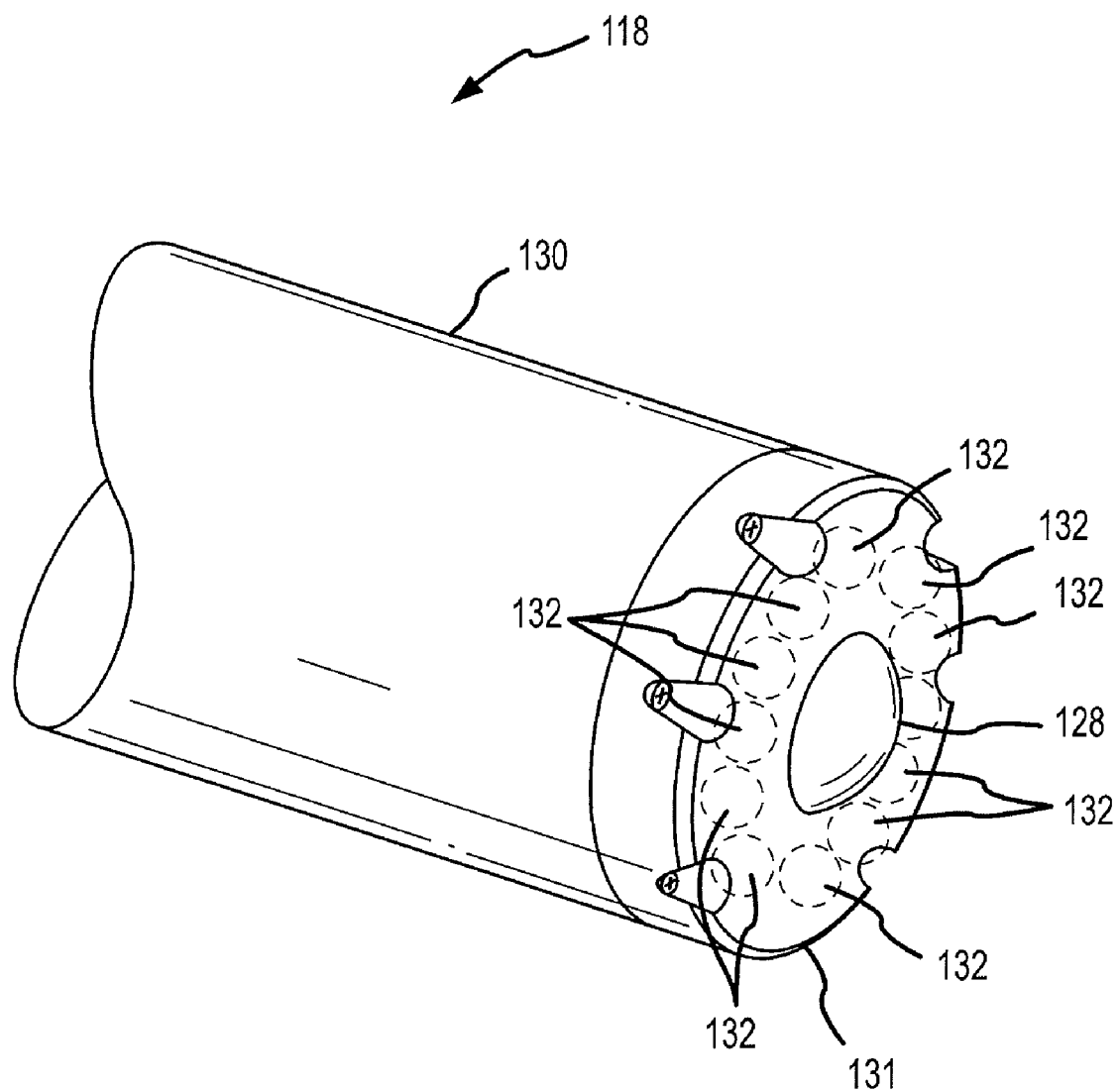
FIG. 2 is a schematic partial isometric view of a distal tip shown in FIG. 1 according to the prior art.
Figure 3:
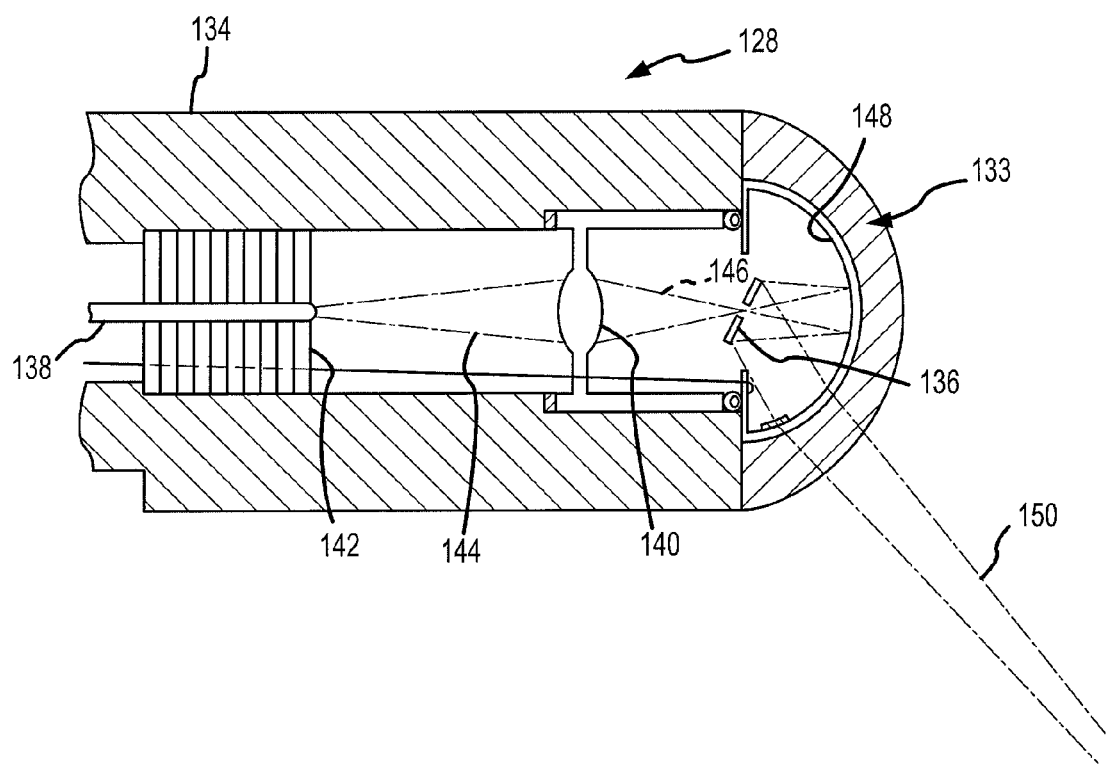
FIG. 3 is a schematic partial side cross-sectional view of the scanning module of FIG. 2 according to the prior art.
Figure 4:
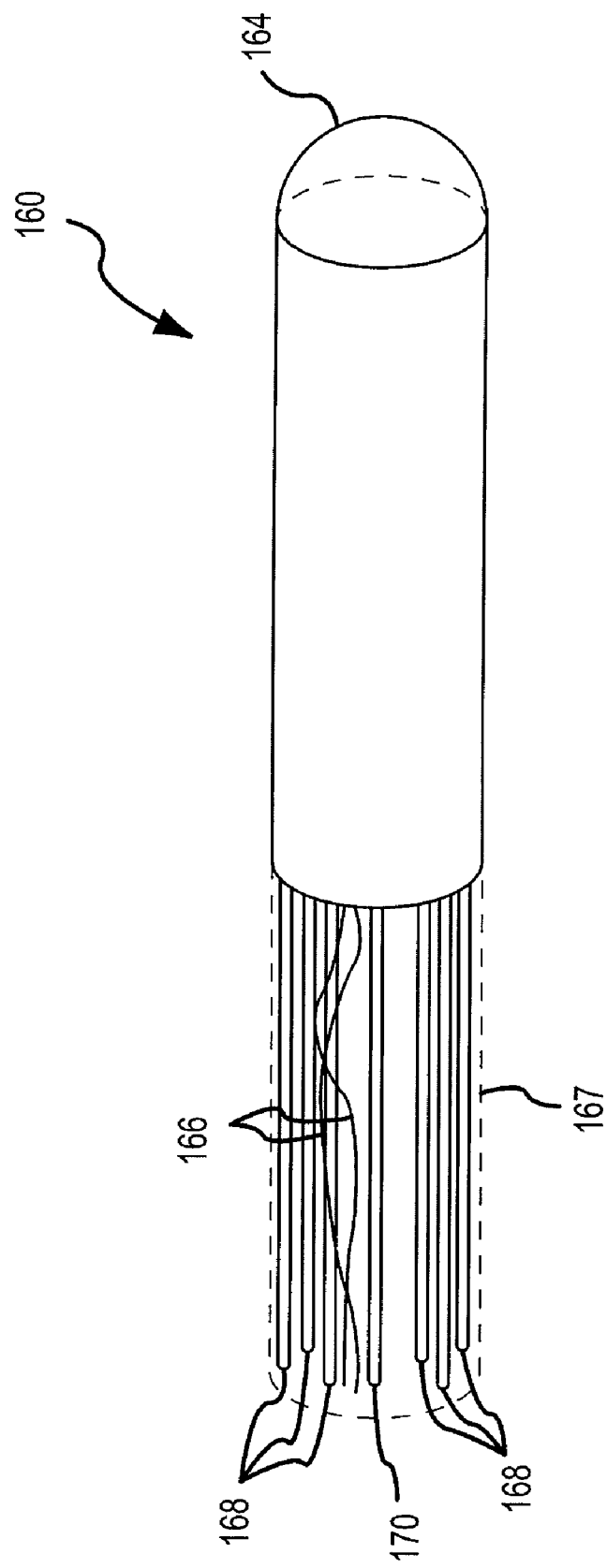
FIG. 4 is a schematic isometric view of a distal tip of an endoscope tip in which the illumination optical fiber is positioned to emit a beam through an opening in a portion of the scanner other than the scan plate according to one embodiment.
Figure 5:
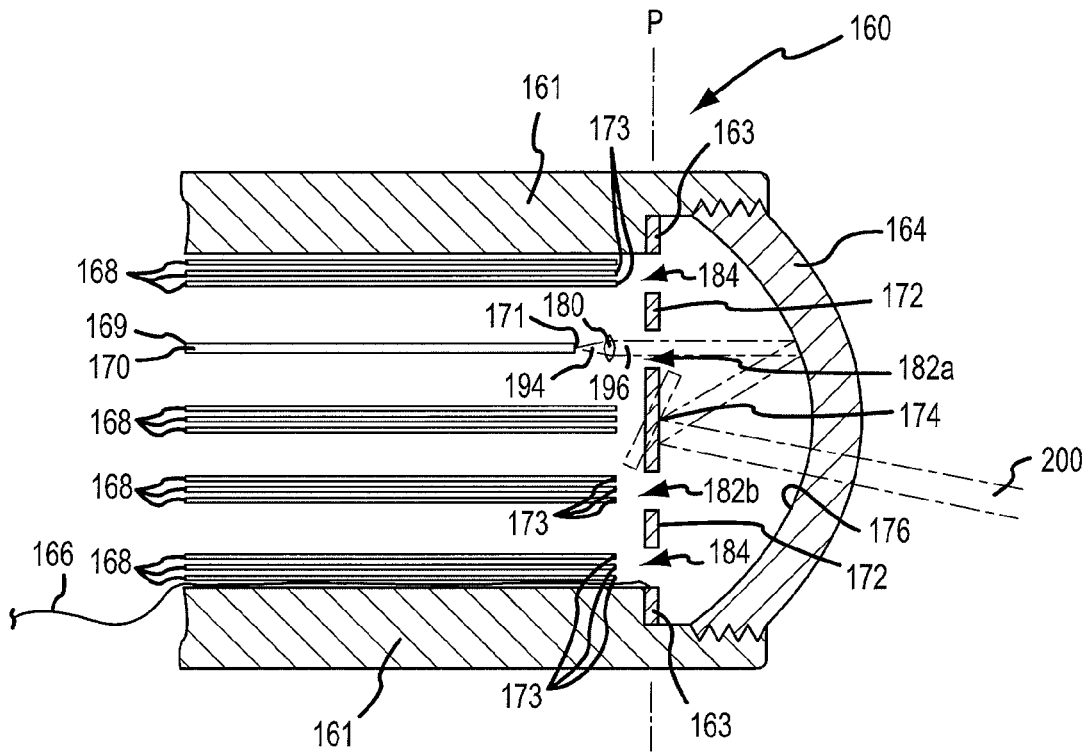
FIG. 5 is a schematic partial side cross-sectional view of the distal tip of FIG. 4.
Figure 6:
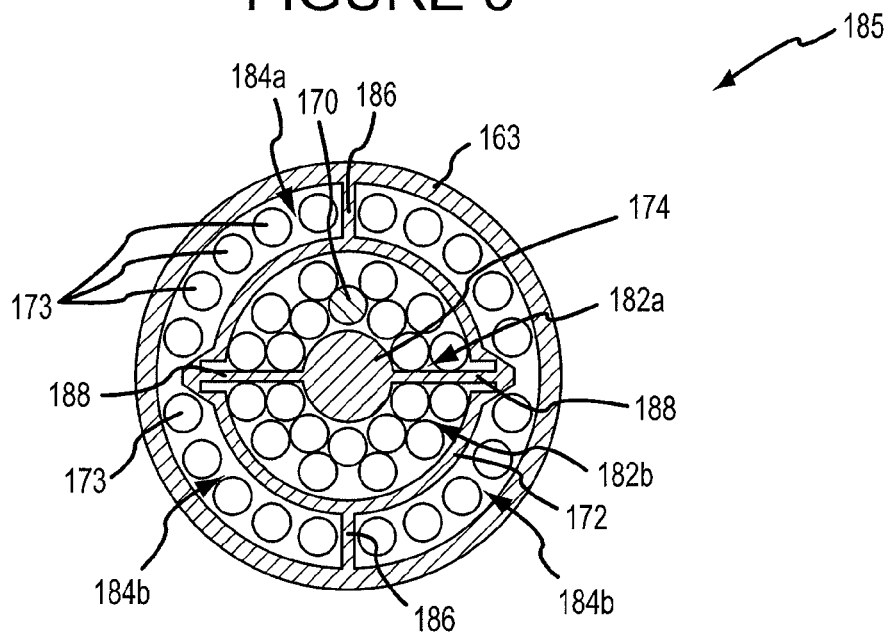
FIG. 6 is a schematic front cross-sectional view of the distal tip of FIGS. 4 and 5.

FIGS. 4 through 6 show one embodiment of distal tip of an endoscope tip for use in a scanned beam endoscope that includes an illumination optical fiber positioned so that light emitted therefrom passes through an opening in the scanner that is not located in the scan plate of the scanners. FIG. 4 shows a schematic isometric view of a distal tip 160 that may form part of or all of an endoscope tip. The distal tip 160 may be attached to the distal end of a hollow body or tube 167 of the endoscope tip that encloses the electrical and optical components thereof, such as wires 166, detection optical fibers 168, and an illumination optical fiber 170. The hollow body 167 may be rigid or flexible depending upon the particular endoscope application.

Turning now to FIGS. 5 and 6, which show the distal tip 160 of FIG. 4 in more detail as schematic partial side and front cross-sectional views, respectively. The distal tip 160 includes a housing 161 that encloses a plurality of the detection optical fibers 168, and an illumination optical fiber 170 having an input end 169 and an output end 171. A dome 164 may be affixed in a suitable manner to the housing 161 for sealing and protect the components of the distal tip 160. The illumination optical fiber 170 may be, for example, a single mode optical fiber. The distal tip 160 also includes a beam shaping optical element 180 configured to shape a beam output from the illumination optical fiber 170 to a selected beam shape and size. In some embodiments, the beam shaping optical element 180 may be a lens, refractive optical element, diffractive optical element, reflective optical element, or combinations thereof, and may be attached to the output end 171 of the illumination optical fiber 170. The distal tip 160 further includes a scanner 185, which may be a MEMS scanner, mounted to interior of the housing 161.

In the particular embodiment for the scanner 185 shown in FIGS. 5 and 6, the scanner 185 has a plurality of openings 182a-182b and 184a-184b. As illustrated, the output end 171 of the illumination optical fiber 170 is positioned behind the opening 182a in the scanner 185. However, the output end 171 of the illumination optical fiber 170 may be positioned behind one of the other openings 182b and 184a-184b, or another opening formed in another portion of the scanner 185. Although a plurality of the detection optical fibers 168 is illustrated in FIGS. 5 and 6, in other embodiments, at least one detection optical fiber 168 may be used. Additionally, although the detection optical fibers 168 are positioned behind the openings 182a-182b and 184a-184b to receive reflected light from the FOV, in other embodiments, the detection optical fibers 168 may be positioned peripherally about the housing 161. In yet another embodiment, the detection optical fibers may be replaced with light detection elements, such as PIN photodiodes or avalanche photodiodes, contained within the distal tip 160.

With continuing reference to FIGS. 5 and 6, instead of having the illumination optical fiber 170 positioned so that a beam emitted from it passes through an aperture in a scan plate 174, the illumination optical fiber 170 is positioned so that the beam 194 emitted from it may be shaped by the beam shaping optical element 180 and passes through an opening in the scanner 185 that is not formed in the scan plate 174. In another embodiment, the beam shaping optical element 180 may be eliminated because the beam size of the beam 194 does not need to be reduced to pass through an aperture formed in the scan plate 174 or the illumination optical fiber 170 is configured to provide the beam 194 with an appropriate beam shape. Depending upon the design of the scanner 185, this may enable reducing the size of the scan plate 174 and, consequently, this may improve the performance characteristics of the scanner 185.

In various embodiment, the scanner 185 may be a 2D MEMS scanner, such as a bulk micro-machined MEMS scanner, a surface micro-machined device, another type of conventional MEMS scanner assembly, or a subsequently developed MEMS scanner assembly. The scanner 185 may be configured to scan one or more beams of light at high speed and in a pattern that covers an entire FOV or a selected portion of a 2D FOV within a frame period. As known in the art, such MEMS scanners may be driven magnetically, electrostatically, capacitively, or combinations thereof. For example, the horizontal scan motion may be driven electrostatically and the vertical scan motion may be driven magnetically. Electrostatic driving may include electrostatic plates, comb drives or the like. Alternatively, both the horizontal and vertical scan may be driven magnetically or capacitively.

FIG. 6 most clearly shows one embodiment for the scanner 185. The scanner 185 includes a scan plate 174 having a reflective surface 175 such as a polished surface or a suitable optical coating. The scan plate 174 is attached to a gimbal ring 172 by torsion arms 188 so that it may rotate about an axis 190 extending through the torsion arms 188. The gimbal ring 172 may also be attached to a frame 163 by torsion arms 186 so that it may rotate about an axis 192 extending through the torsion arms 186. Although not shown, it should be understood that the scanner 185 may include drive components common to MEMS scanners, such as drive circuitry and actuation components, for effecting rotation of the scan plate 174 about the axes 190 and 192. The scan plate 174 may also includes an aperture 178 extending through its thickness that is generally aligned with the output end 171 of the illumination optical fiber 170 to receive a beam of light shaped to a selected beam diameter by the beam shaping optical element 180 that can pass through the aperture 178.

The scanner 185 may include a plurality of openings formed therein. The openings 182a and 182b are defined by the gimbal ring 172, and the scan plate 174 and its associated torsion arms 188. The openings 184a and 184b are formed in the scanner 185 and are defined by the frame 163, and the gimbal ring 172 and its associated torsion arms 188. As best shown in FIG. 6, the output end 171 of the illumination optical fiber 170 may be positioned aft of major plane P of the scanner 185 such that light emitted therefrom through the openings 182a-182b and 184a-184b.

The dome 164 may include a partially reflective interior reflective surface 176 for redirecting light emitted from the illumination optical fiber 170 to the scanner 185 and allowing light scanned from the scanner 185 to pass therethrough. In some embodiments, the dome 164 may be configured to provide optical power for shaping light it reflects to the scanner 185 and light scanned from the scanner 185 that passes through the dome 164. One embodiment of a suitable dome 164 is disclosed in the aforementioned '540 application. Such a dome is configured to selectively reflect and transmit light having a particular polarization direction. In other embodiments, the dome 164 may not have any optical power and a fixed intermediate reflective structure may be disposed between the surface 176 and the scanner 185.

In operation, light may be input into the input end 169 of the illumination optical fiber 170 using a light source (not shown) and emitted from the output end 171 of the illumination optical fiber 170 as beam 194. The beam 194 may be received by the beam shaping optical element 180, which is configured to focus the beam 194 to a selected shaped beam 196 that has a beam diameter smaller than the opening 182a in the scanner 185 through which it passes. After shaping and passing through the opening 182a, the shaped beam 196 is reflected from an interior reflective surface 176 of the dome 164 to the reflective surface 175 of the scanner 185. As previously discussed above, the dome 164 may be configured to partially or fully collimate the shaped beam 196. Then, the scanner 185 and its associated reflective surface 175 scans the shaped beam 196 as a scanned beam 200 across the FOV. As the scanned beam 200 passes through the dome 164, it may be further shaped to a selected beam shape such as a selected beam waist distance from the end of the dome 164. The scanned beam 200 is reflected off of the interior of a body cavity in which the distal tip 160 is positioned in. The reflected light (e.g., specular reflected light and diffuse reflected light also referred to as scattered light) from the FOV passes through the dome 164 and is received by respective collection ends 173 of the detection optical fibers 168 that are selectively positioned to receive the reflected light through one or more openings in the scanner 185. Optical signals representative of characteristics of the FOV may be further processed to define an image.

Figure 7:
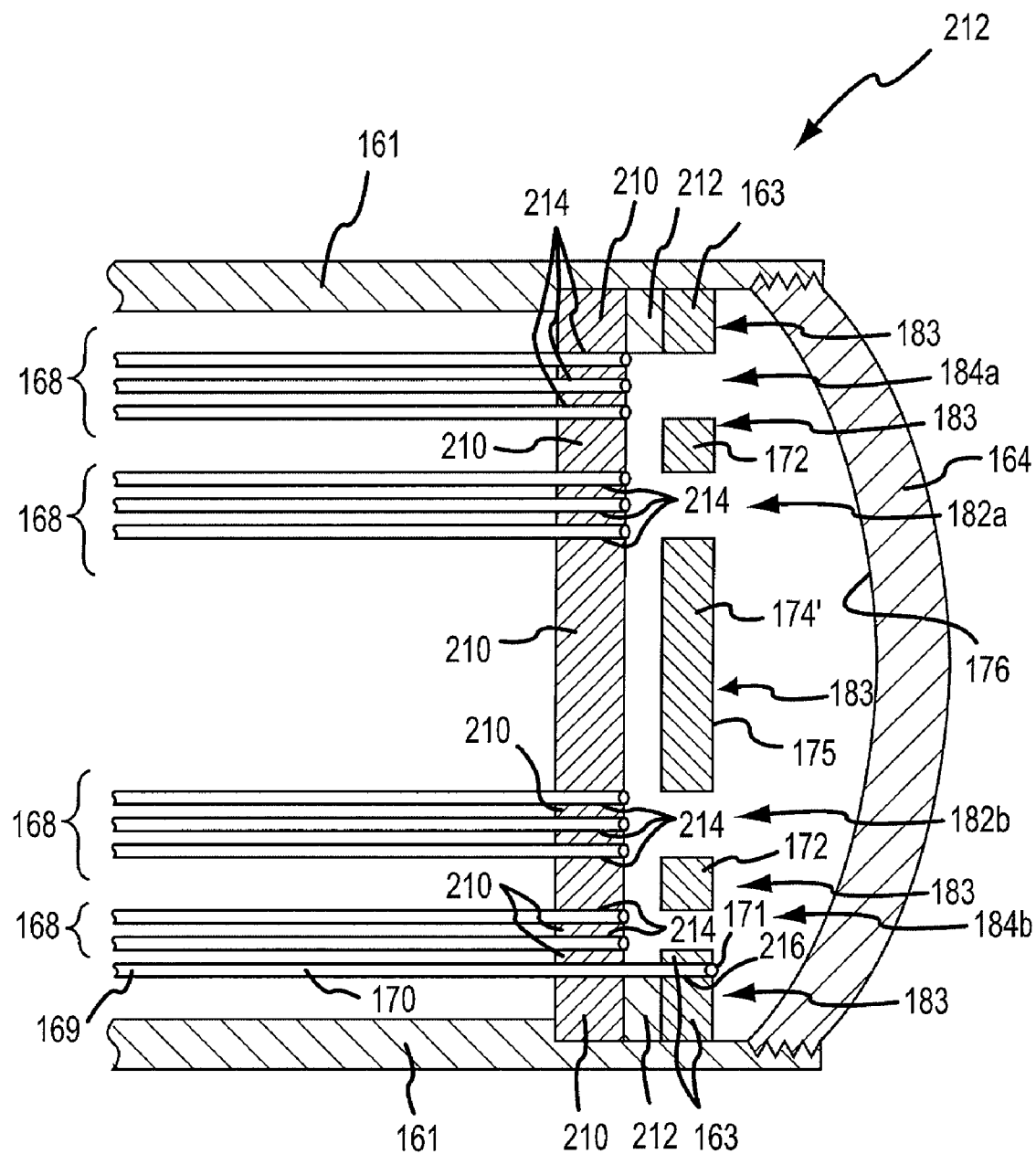
FIG. 7 is a schematic partial side cross-sectional view of a distal tip of an endoscope tip having a handle substrate bonded to the scanner in which vias are formed at least through the handle substrate for selectively positioning the optical fibers according to another embodiment.
Figure 8:
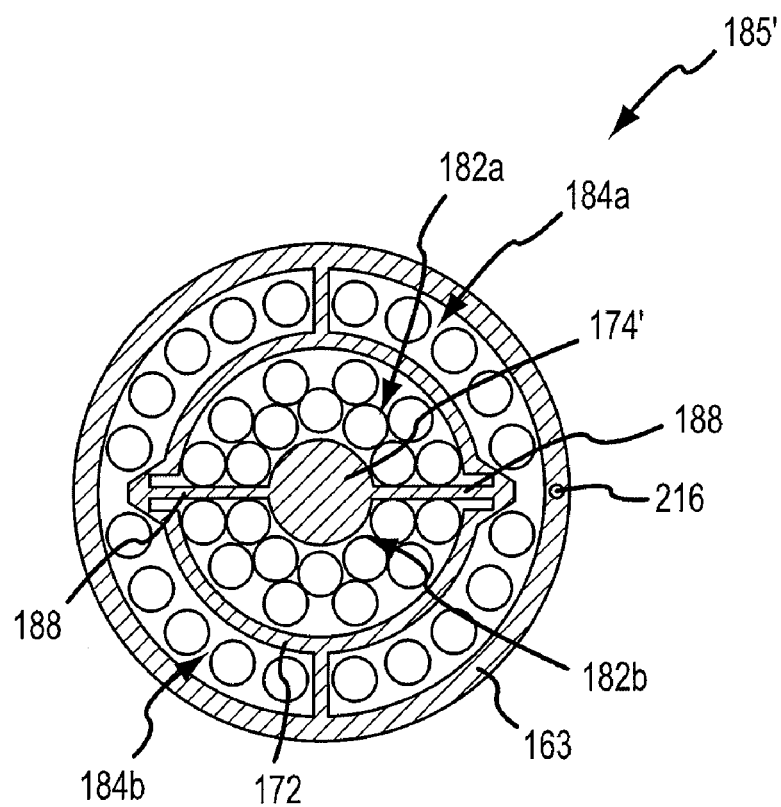
FIG. 8 is a schematic front cross-sectional view of the distal tip of FIG. 7.

FIGS. 7 and 8 show schematic side and front cross-sectional views, respectively, of another embodiment of a distal tip 212 in which a scanner 185' is bonded to a handle substrate that is used as a ferrule for the illumination optical fiber 170 and/or the detection optical fibers 168. Handle substrates are used to support another substrate that, typically, MEMS scanners are fabricated from. The embodiments described with respect to FIGS. 7 and 8 may employ photolithographically formed vias within the handle substrate to position the illumination optical fibers and detection optical fibers in selected positions relative to the scanner. The distal tip 212 has many of the same components that are included in the distal tip 160 of FIGS. 5 and 6. Therefore, in the interest of brevity, the components of the distal tips 160 and 212 that correspond to each other have been provided with the same or similar reference numerals, and an explanation of their structure and operation will not be repeated.

According to one embodiment shown in FIGS. 7 and 8, the scanner 185' is bonded to the handle substrate 210. One embodiment of a suitable bonding method is by oxidizing a silicon substrate in which the scanner 185' is formed in and oxidizing a silicon handle substrate 210. The oxidized silicon substrate and the oxidized silicon handle substrate 210 may be bonded together by fusion bonding the oxidized layers of each substrate together, collectively shown as layer 212, prior to forming the scanner 185 within the silicon substrate.

The handle substrate 210 may have a plurality of vias 214 formed therein that extend completely through the thickness of the handle substrate 210. Positioned within each of the vias 214 is one of the detection optical fibers 168. The detection optical fibers 168 may be positioned behind the openings 182a-182b and 184a-184b within the scanner 185'. However, in another embodiment, the vias 214 may be formed in another portion of the scanner 185'. Extending through the thickness of the scanner 185' and the handling substrate 210 is a via 216, which may be offset from the center of the scanner 185', having the illumination optical fiber 170 positioned therein. The illumination optical fiber 170 and the detection optical fiber 168 may be bonded to the interior walls of the vias 214 and 216 using a suitable adhesive, such as an epoxy. Although at least a portion of the output end 171 of the illumination optical fiber 170 is shown positioned generally coplanar with upper surface of the frame 163 of the scanner 185', the output end 171 may extend past the upper surface of the frame 163 to project out of the via 216. In another embodiment, the output end 171 may be positioned a distance below the upper surface of the frame 163. In such an embodiment, the diameter of the via 216 should be larger than the beam of light emitted from the illumination optical fiber 170. In yet another embodiment, the output end 171 is positioned below the upper surface of the frame 163, and a beam shaping optical element, such as the beam shaping optical element 180, may be positioned within the via 216 to shape the light emitted from the illumination optical fiber 170 to a beam diameter smaller than the diameter of the via 216. In other embodiments, the via 216 does not extend through any portion of the scanner 185', and the via 216 may be located within the handle substrate 210 so that the illumination optical fiber 170 is located behind one of the openings 182a-182b and

184*a*-184*b* so that light emitted from the output end 171 of the illumination optical fiber 170 passes through one of the openings 182*a*-182*b* and 184*a*-184*b*. Accordingly, the vias 214 and 216 may be formed with photolithographic precision to enable accurately and selectively positioning the illumination optical fiber, the detection optical fibers, or both within the handle substrate.

In one embodiment, the output end 171 of the illumination optical fiber 170 and the collection end 173 of the detection optical fibers 168 may be prepared (e.g., cleaving and polishing) prior to insertion into their respective vias 214 and 216. In another embodiment, the illumination optical fiber 170 and the detection optical fibers 168 may be inserted into and bonded within their respective vias 214 and 216 so that the ends thereof project out of them, and the illumination optical fiber 170 and the detection optical fiber 168 may be cleaved and polished, as needed, when assembled with the scanner 185' and the handle substrate 210.

Figure 9:
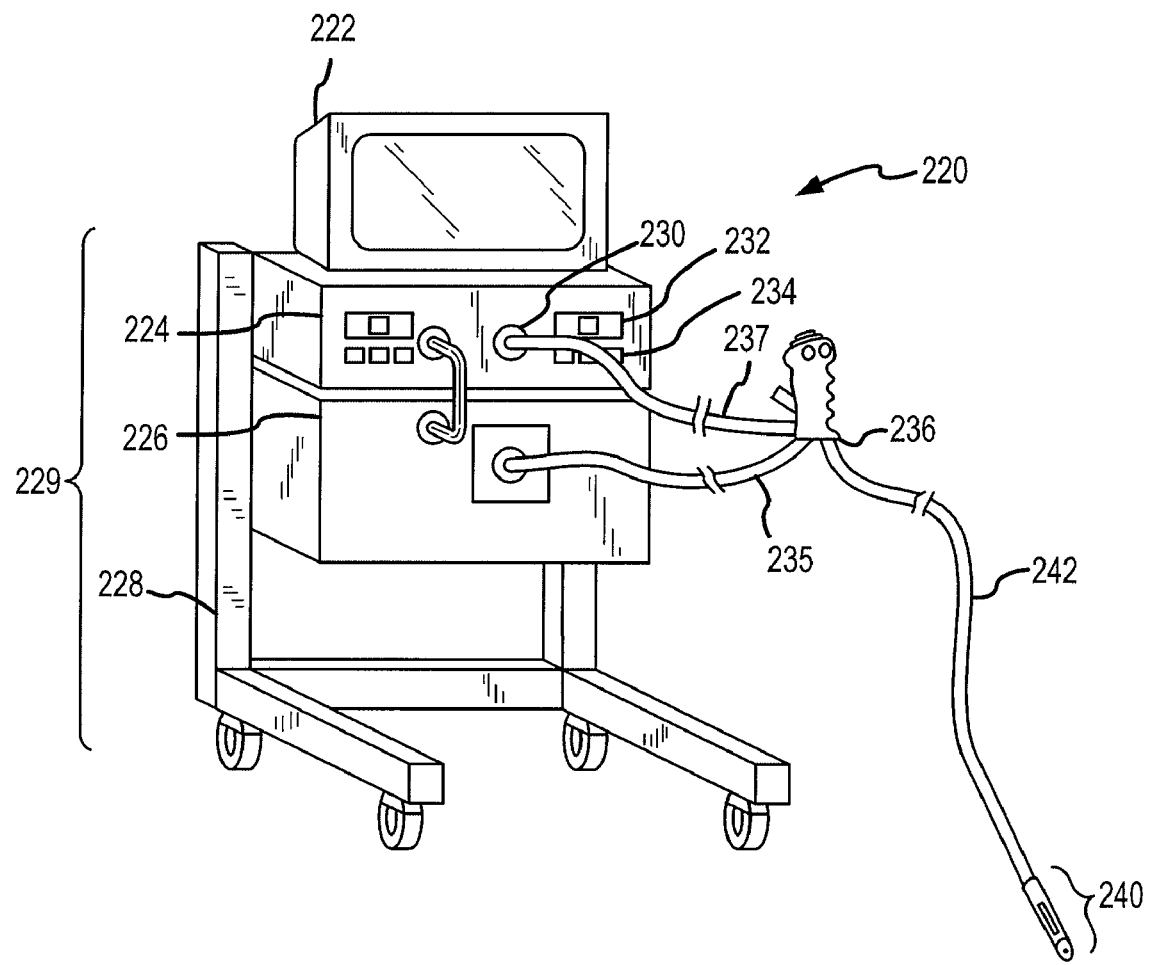
FIG. 9 is schematic drawing of a scanned beam endoscope that may utilize any of the distal tips disclosed herein according to one embodiment.

FIG. 9 shows a schematic drawing of a scanned beam endoscope 220 according to one embodiment that may utilize any of the aforementioned embodiments of distal tips. The scanned beam endoscope 220 includes a control module 224, monitor 222, and optional pump 226, all of which may be mounted on a cart 228, and collectively referred to as console 229. The console 229 may communicate with a handpiece 236 through an external cable 237, which is connected to the console 229 via connector 230. The handpiece 236 may be operably coupled to the pump 226 and an endoscope tip 242. The handpiece 236 controls the pump 226 in order to selectively pump irrigation fluid through a hose 235 and out of an opening of the endoscope tip 242. The endoscope tip 242 includes a distal tip 240, which may be any of the aforementioned embodiments of distal tips. The endoscope tip 242 encloses components, such as optical fibers and electrical wiring, and, optionally, other components such as an irrigation channel, a working channel, and a steering mechanism.

In operation, the distal tip 240 is placed within a body cavity. Responsive to user input via the handpiece 236, the distal tip 240 scans light over the FOV. Reflected light from the interior of the body cavity is collected by the distal tip 240. A signal representative of an image of the internal surfaces is sent from the distal tip 240 to the console 229 for viewing on the monitor 222 and diagnosis by the medical professional.

Figure 10:
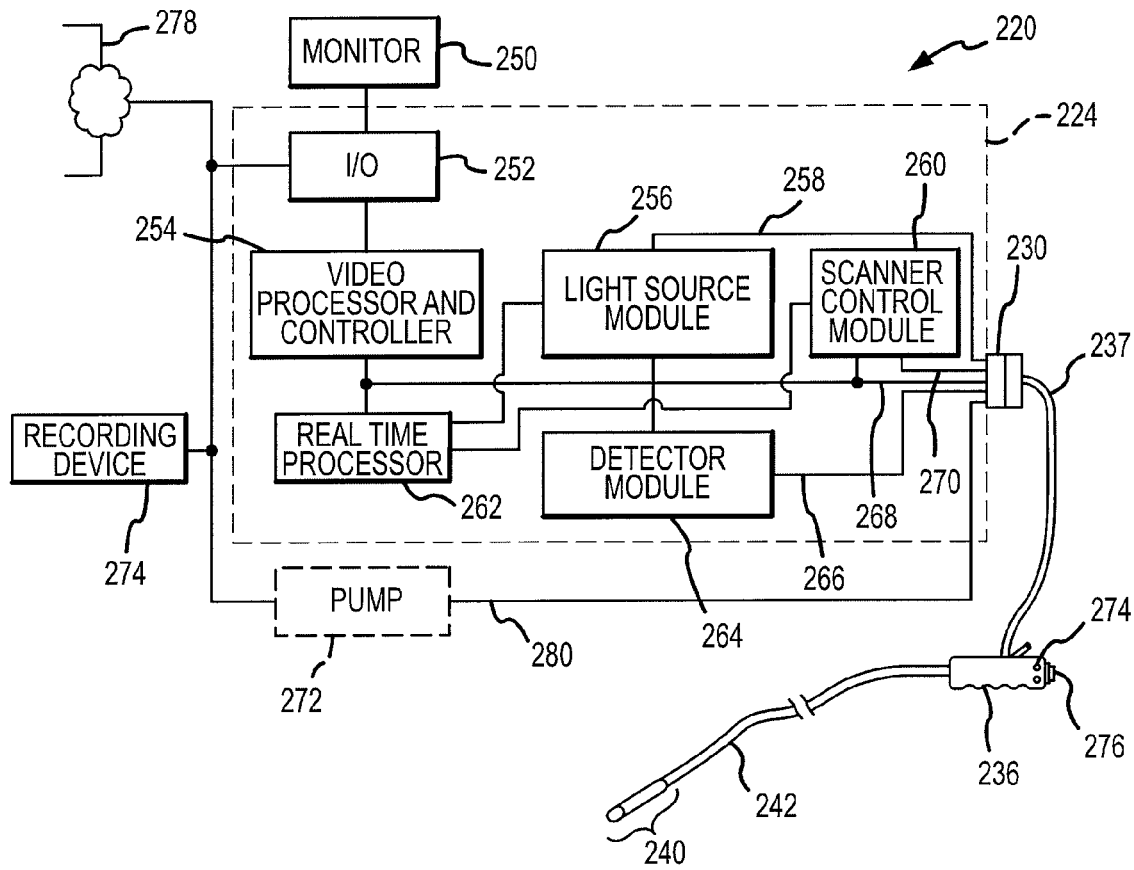
FIG. 10 is a block diagram illustrating the relationship between the various components of the scanned beam endoscope of FIG. 9 according to one embodiment.

FIG. 10 is a block diagram illustrating the relationships between various components of the endoscope 220. The control module 224 contains a number of logical and/or physical elements that cooperate to produce an image on the monitor 222. The control module 224 includes a video processor and controller 254 that receives and is responsive to control inputs by the user via the handpiece 236. The video processor and controller 254 may also include image processing functions. The user control inputs are sent to the video processor and controller 254 via a control line 268.

The video processor and controller 254 also controls the operation of the other components within the control module 224. The control module 224 further includes a real time processor 262, which may, for example, be embodied as a PCI board mounted on the video processor and controller 254. The real time processor 262 is coupled to a light source module 256, a scanner control module 260, a detector module 264, and the video processor and controller 254. The scanner control module 260 is operable to control the scanner of the distal tip 240 and the detector module 264 is configured for detecting light reflected from the FOV.

The light source module 256, which may be housed separately, includes one or more light sources that provides the light energy used for beam scanning by the distal tip 240. Suitable light sources for producing polarized and/or non-polarized light include light emitting diodes, laser diodes, and diode-pumped solid state (DPSS) lasers. Such light sources may also be operable to emit light over a range of wavelengths.

Responsive to user inputs via the handpiece 236, a control signal is sent to the video processor and controller 254 via the control line 268. The video processor and controller 254 transmits instructions to the real time processor 262. Responsive to instructions from the real time processor 262, light energy is output from the light source module 256 to the distal tip 240 via an optical fiber 258. The optical fiber 258, which is optically coupled to the external cable 237 via the connector 230, transmits the light to the external cable 237. The light travels through the handpiece 236 to the endoscope tip 242 and is ultimately scanned across the FOV. Light reflected from the FOV is collected at the distal tip 240 and a representative signal is transmitted to the controller module 224.

In some embodiments, the representative signal transmitted to the control module 224 is an optical signal. Thus, a return signal line 266 may be an optical fiber or an optical fiber bundle that is coupled to the detector module 264 and transmit the representative optical signal to the detector module 264. At the detector module 264, the optical signals corresponding to the FOV characteristics are converted into electrical signals and returned to the real time processor 262 for real time processing and parsing to the video processor and controller 254. Electrical signals representative of the optical signals may be amplified and optionally digitized by the detector module 264 prior to transmission to real time processor 262. In an alternative embodiment, analog signals may be passed to the real time processor 262 and analog-to-digital conversion performed there. It is also contemplated that the detector module 264 and the real time processor 262 may be combined into a single physical element.

In other embodiments, reflected light representative of the FOV may be converted into electrical signals at the endoscope tip 242 or the distal tip 240 by one or more photodetectors such as PIN photodiodes, avalanche photodiodes (APDs), or photomultiplier tubes. In such an embodiment, the return line 266 may be electrical wires and the detector module 264 may be omitted.

The video processor and controller 254 has an interface 252 that may include several separate input/output lines. A video output may be coupled to the monitor 222 for displaying the image. A recording device 274 may also be coupled to the interface 252 to capture video information recording a procedure. Additionally, in some embodiments, the endoscope system 220 may be connected to a network or the Internet 278 for remote expert input, remote viewing, archiving, library retrieval, or the like. In another embodiment, the video processor and controller 254 may optionally combine data received via the interface 252 with image data and the monitor 222 with information derived from a plurality of sources including the endoscope tip 242.

In another embodiment, in addition to or as an alternative to the monitor 222, the image may be output to one or more remote devices such as, for example, a head mounted display. In such an embodiment, context information such as viewing perspective may be combined with FOV and/or other information in the video processor and controller 254 to create context-sensitive information display.

From the foregoing it will be appreciated that, although specific embodiments of the invention have been described herein for purposes of illustration, various modifications may be made without deviating from the spirit and scope of the invention. For example, the teachings disclosed herein are generally applicable for use in scanned beam imagers such as bar code scanners in addition to scanned beam endoscopes. Accordingly, the invention is not limited except as by the appended claims.

What is claimed is:

1. A scanned beam endoscope, comprising:
a light source operable to provide light;
an endoscope tip, comprising:
   an illumination optical fiber having an output end and an input end coupled to the light source;
   a scanner having a scan plate positioned to receive a beam output from the output end of the illumination optical fiber and operable to scan the beam across a field-of-view (FOV), the scanner having at least one opening located in a portion of the scanner other than the scan plate, the output end of the illumination optical fiber positioned so that the beam output therefrom passes through the at least one opening; and
   at least one light detection element positioned to receive reflected light from the FOV and positioned in at least one of the at least one openings; and
a display coupled to the at least one light detection element, the display operable to show an image characteristic of the FOV.

2. The scanned beam endoscope of claim 1 wherein the at least one light detection element comprises a plurality of photodiodes positioned to receive the reflected light from the FOV.

3. The scanned beam endoscope of claim 1:
wherein the at least one light detection element comprises at least one detection optical fiber positioned to receive the reflected light from the FOV and transmit optical signals characteristic of the FOV;
further comprising a converter operable to convert the optical signals to electrical signals; and
wherein the display is coupled to the converter to receive the electrical signals.

4. The scanned beam endoscope of claim 1 wherein the output end of the illumination optical fiber is positioned aft of a major plane of the scanner.

5. The scanned beam endoscope of claim 1 wherein:
the at least one opening comprises a plurality of openings;
the scanner defines the plurality of openings; and
the output end of the illumination optical fiber is positioned so that the beam output therefrom passes through the one of the openings.

6. The scanned beam endoscope of claim 1 wherein:
the at least one opening comprises a plurality of openings;
the scanner comprises:
   a frame;
   a gimbal attached to the frame by first and second gimbal torsion arms, first and second openings of the plurality of openings being defined by the frame, gimbal, and first and second gimbal torsion arms; and
   a scan plate having a reflective surface, the scan plate attached to the gimbal by first and second scan plate torsion arms, third and fourth openings of the plurality of openings defined by the gimbal, scan plate and first and second scan plate torsion arms; and
the output end of the illumination optical fiber is positioned so that the beam output therefrom passes through the one of the openings.

7. The scanned beam endoscope of claim 1 wherein:
the at least one opening comprises a plurality of openings;
the scanner defines the plurality of openings; and
the at least one light detection element comprises a plurality of detection optical fibers, each of the detection optical fibers being positioned to receive the reflected light from the FOV through at least one of the openings in the scanner.

8. The scanned beam endoscope of claim 1 wherein the endoscope tip comprises a beam shaping optical element positioned to receive the beam output from the output end of the illumination optical fiber, the beam shaping optical element operable to shape the beam to a selected beam size.

9. The scanned beam endoscope of claim 1 wherein the endoscope tip comprises a dome positioned to receive the beam scanned by the scanner and configured to shape the beam scanned by the scanner.

10. The scanned beam endoscope of claim 1 wherein the endoscope tip comprises a dome positioned to receive the beam scanned by the scanner, the dome configured to reflect and transmit light having a particular polarization direction.

11. The scanned beam endoscope of claim 1 wherein the scanner comprises a MEMS scanner.

12. An endoscope tip, comprising:
an illumination optical fiber having an output end and an input end coupled to a light source;
a scanner having a scan plate positioned to receive a beam output from the output end of the illumination optical fiber and operable to scan the beam across a field-of-view (FOV), the scanner having at least one opening located in a portion of the scanner other than the scan plate, the output end of the illumination optical fiber positioned so that the beam output therefrom passes through the at least one opening; and
at least one light detection element positioned to receive reflected light from the FOV and positioned in at least one of the at least one openings.

13. The endoscope tip of claim 12 wherein the at least one light detection element comprises a plurality of photodiodes positioned to receive the reflected light from the FOV through the plurality of openings in the scanner.

14. The endoscope tip of claim 12:
wherein the at least one light detection element comprises at least one detection optical fiber positioned to receive the reflected light from the FOV and transmit optical signals characteristic of the FOV;
further comprising a converter operable to convert the optical signals to electrical signals; and
wherein the display is coupled to the converter to receive the electrical signals.

15. The endoscope tip of claim 12 wherein the output end of the illumination optical fiber is positioned aft of a major plane of the scanner.

16. The endoscope tip of claim 12 wherein:
the at least one opening comprises a plurality of openings;
the scanner defines the plurality of openings; and
the output end of the illumination optical fiber is positioned so that the beam output therefrom passes through the one of the openings.

17. The endoscope tip of claim 12 wherein:
the at least one opening comprises a plurality of openings;
the scanner comprises:
   a frame;
   a gimbal attached to the frame by first and second gimbal torsion arms, first and second openings of the plurality of openings being defined by the frame, gimbal, and first and second gimbal torsion arms; and
   a scan plate having a reflective surface, the scan plate attached to the gimbal by first and second scan plate torsion arms, third and fourth openings of the plurality of openings defined by the gimbal, scan plate and first and second scan plate torsion arms; and the output end of the illumination optical fiber is positioned so that the beam output therefrom passes through the one of the openings.

18. The endoscope tip of claim 12 wherein:

the at least one opening comprises a plurality of openings;

the scanner defines the plurality of openings; and the at least one light detection element comprises a plurality of detection optical fibers, each of the detection optical fibers being positioned to receive the reflected light from the FOV through at least one of the openings in the scanner.

19. The endoscope tip of claim 12, further comprising a beam shaping optical element positioned to receive the beam output from the output end of the illumination optical fiber, the beam shaping optical element operable to shape the beam to a selected beam size.

20. The endoscope tip of claim 12, further comprising a dome positioned to receive the beam scanned by the scanner and configured to shape the beam scanned by the scanner.

21. The endoscope tip of claim 12, further comprising a dome positioned to receive the beam scanned by the scanner, the dome configured to reflect and transmit light having a particular polarization direction.

22. The endoscope tip of claim 12 wherein the scanner comprises a MEMS scanner.

* * * * *